United States Patent [19]

Liu et al.

[11] Patent Number: 4,937,360
[45] Date of Patent: Jun. 26, 1990

[54] N-SUBSTITUTED AMIDE DERIVATIVES USEFUL FOR TREATING LIVER DISEASES

[75] Inventors: Geng-tao Liu; Liang Huang; Er-chang Rao; Jin Zhou; Yan Li, all of Beijing, China; Katsuo Hatayama, Omiya, Japan; Tatsuhiko Sano, Omiya, Japan; Kensei Yoshikawa, Urawa, Japan; Shohei Higuchi, Kitamoto, Japan; Iwao Arai, Ageo, Japan

[73] Assignees: Taisho Pharmaceutical Co., Ltd., Japan; The Institute of Materia Medica of Chinese Academy of Medical Sciences, China

[21] Appl. No.: 373,338

[22] Filed: Jun. 28, 1989

[30] Foreign Application Priority Data

Jul. 8, 1988 [JP] Japan .................. 63-170727

[51] Int. Cl.$^5$ ............................................ C07D 317/54
[52] U.S. Cl. ..................................... 549/436; 549/441
[58] Field of Search ............................. 549/441, 436

[56] References Cited

FOREIGN PATENT DOCUMENTS 332474 2/1921 Fed. Rep. of Germany ...... 549/441
1204195 9/1970 United Kingdom ................ 549/436

Primary Examiner—Nicky Chan
Attorney, Agent, or Firm—Lorusso & Loud

[57] ABSTRACT

N-substituted amide derivative represented by the formula

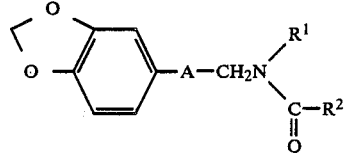

wherein A is —CH(OH)— or —C(=O)—, $R^1$ is a hydrogen atom or an alkyl group having 1 to 3 carbon atoms, and $R^2$ is an alkyl group having 1 to 6 carbon atoms, are disclosed. These compounds are useful for prevention and therapy for liver diseases.

7 Claims, No Drawings

N-SUBSTITUTED AMIDE DERIVATIVES USEFUL FOR TREATING LIVER DISEASES

BACKGROUND OF THE INVENTION

1. FIELD OF THE INVENTION

The present invention relates to novel N-substituted amide derivatives useful in the field of medicines, and especially for prevention and therapy for liver diseases.

2. DESCRIPTION OF THE PRIOR ART

The liver suffers acute or chronic injuries such as, for example, fatty liver, jaundice and hepatic cirrhosis by various reasons such as virus, alcohol, malnutrition and hepatic circulation injuries. Malutilate and the like are recently reported as a therapeutic agent for these liver diseases. However, there have not been found actually effective therapy and therapeutic agents including symptomatic therapy such as dietetic therapy, and drug therapy by administration of steroids or immunoactivators.

As stated above, there has not yet been any satisfactory therapy for liver diseases, especially delayed and chronic diseases. In addition, drug therapy by administration of steroids and immunoactivators has a problem which side-effects of the drugs are serious.

As a result of synthesis of various N-substituted amide derivatives to develop the therapeutical agents of liver diseases for solving the above problem, the present inventors have found that certain compounds show remarkable inhibition reaction against liver injuries in experimental liver injury models, and have completed the present invention.

An object of the present invention is to provide an N-substituted amide derivative represented by the formula

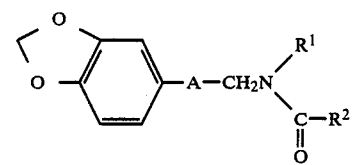

wherein A is —CH(OH)— or —C(=O)—, $R^1$ is a hydrogen atom or an alkyl group having 1 to 3 carbon atoms, and $R^2$ is an alkyl group having 1 to 6 carbon atoms.

In the present invention, the alkyl group may be straight or branched chained alkyl group such as, for example, a methyl group, an ethyl group, a n-propyl group, an isopropyl group, a n-butyl group, an isobutyl group, a n-hexyl group and the like.

Examples of typical compound of the present invention are N-(3,4-methylenedioxyphenacyl)acetamide, N-methyl-N-(3,4-methylenedioxyphenacyl)-n-hexanamide, N-(3,4-methylenedioxyphenacyl)-n-butanamide, N-(3,4-methylenedioxyphenacyl)-n-hexanamide and N-methyl-N-(β-hydroxy-3,4-methylenedioxyphenethyl)acetamide.

The compounds of the present invention can be prepared, for example, by the processes showing by the following reaction schemes (wherein $R^1$ and $R^2$ are as defined above, and X and X' are each a halogen atom).

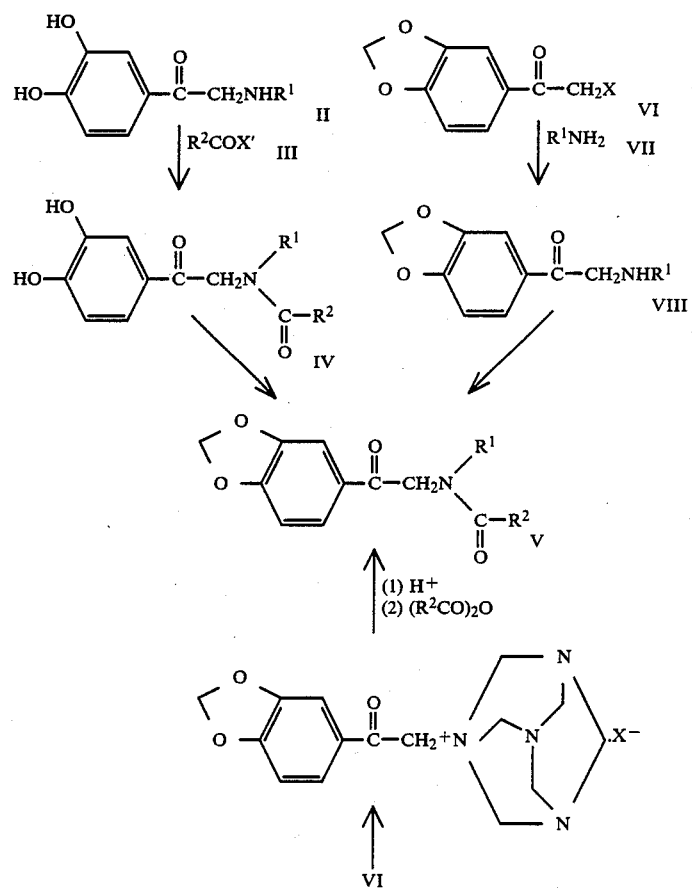

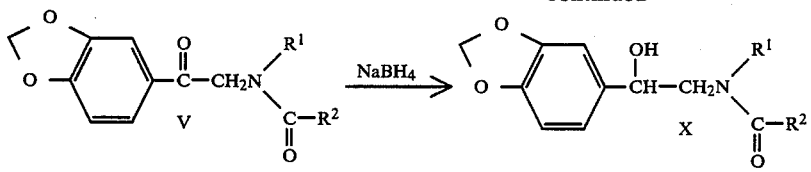

Process 1: An amine of Formula II is reacted with an acid halide of Formula III in an organic solvent to give an amide derivative of Formula IV. Examples of the organic solvent used in the reaction are halogenated hydrocarbon such as chloroform and dichloromethane, and ethers such as ethyl ether, dioxane and tetrahydrofuran. The reaction temperature is from −10° C. to the boiling point of the solvent, and preferably from 0° C. to room temperature. The reaction can be thoroughly finished in about an hour.

Then, the compound of Formula IV is reacted with a dihalomethane in an organic solvent or without solvent in the presence of a base to give the compound of Formula V of the present invention. The dihalomethane may be dichloromethane, dibromomethane and the like. Examples of the organic solvent used are N,N-dimethylformamide, dimethyl sulfoxide and the like. The reaction temperature is from room temperature to the boiling point of the solvent. The reaction time can be recognized by observing the disappearance of the material by means of silica gel thin layer chromatography and the like.

Process 2: An α-halogenoacetophenone compound of Formula VI is reacted with an amine of Formula VII in a solvent to give an amino derivative of Formula VIII. Examples of the solvent used in the reaction are alcohols such as methanol and ethanol; ethers such as ethyl ether, dioxane and tetrahydrofuran; acetone, benzene, water and the like. The reaction temperature is from −10° C. to the boiling point of the solvent, and preferably from 0° C. to room temperature. The reaction is momentarily finished, but it may be carried out with stirring for 0.5 to 2 hours.

Then, the resulting amino derivative of Formula VIII can be converted to the compound of Formula V of the present invention by an ordinary acylation. Examples of the ordinary acylation are those carried out using acylating agents such as acid anhydrides (e.g., acetic anhydride, propionic anhydride, butyric anhydride and the like) in the presence of a base; those carried out using acylating agents such as acid halides (e.g., acetyl chloride, propionyl bromide, hexanoyl chloride and the like); those carried out by condensing with ethyl acetate, ethyl propionate, methyl butyrate and the like; and those carried out by condensing with carbonic acid derivatives such as acetic acid, propionic acid, butyric acid and the like in the presence of a condensing agent (e.g., dicyclohexylcarbodiimide, diethyl azodicarboxylate and the like). The reaction may be carried out by using a solvent such as, for example, pyridine, N,N-dimethylformamide, dimethyl sulfoxide, ethyl ether, benzene, toluene, water and the like. Examples of the base used in the reaction are sodium carbonate, potassium carbonate, sodium hydrogen carbonate, sodium hydroxide, pyridine, triethylamine and the like. The reaction temperature and reaction time are the same as those of an ordinary acylation.

Process 3: The α-halogenoacetophenone compound of Formula VI is reacted with hexamethylenetetramine in a solvent to give a quaternary ammonium salt of formula IX. The solvents used in this reaction are preferably halogenated hydrocarbons such as chloroform, dichloromethane and the like.

Then, the quaternary ammonium salt of Formula IX is decomposed by adding a mineral acid such as hydrochloric acid in an alcohol such as methanol and ethanol to give a primary ammonium salt, which is then subjected to an acylation similar to that of Process 2 to give a compound of Formula V wherein $R^1$ is a hydrogen atom of the present invention.

Process 4: A compound of Formula I wherein A is —CH(OH)— of the present invention can be prepared by a reduction of the compound of Formula V of the present invention obtained above with sodium borohydride in a solvent. The solvents used in this reaction are preferably alcohols such as methanol and ethanol, and ethers such as ethyl ether and tetrahydrofuran.

The compounds of the present invention inhibit serum GPT activity remarkably in experimental liver injury models, and therefore have an excellent inhibition effect on liver injuries. Accordingly, the compounds of the present invention are useful as prevention or therapeutic agents of liver injuries such as chronic hepatitis and hepatic cirrhosis. For the purposes, these compounds can be administered by oral route or by parenteral route such as intravenous, intramuscular, subcutaneous and percutaneous route. The dosage form of oral administration are tablets, capsules, granules, pills and the like, all of which may be prepared by known methods. For example, granules may be prepared using mannitol and corn starch as fillers, and hydroxypropylcellulose as a binder; and tablets may be prepared using crystalline cellulose and lactose as fillers, carboxymethylcellulose calcium as a disintegrator, polyvinylpyrrolidone as a binder and magnesium stearate as a lubricant. The dosage forms of parenteral administration are injectional preparations, ointments and the like, all of which may be prepared by ordinary manners.

The dose of the compound of the present invention depends on the compounds, administration route and severity of diseases, but usually it is in the range from 0.5 to 10 mg/kg/day.

The present invention is illustrated in more detail by the following Exampels.

EXAMPLE 1

Preparation of N-methyl-N-(3,4-methylenedioxyphenacyl)acetamide

To a suspension of 33 g (0.15 mole) of adrenalone hydrochloride in 30 ml of chloroform cooled to 0° to 2° C. under a nitrogen atmosphere was added 225 ml of 2N aqueous sodium hydroxide solution. Then, 75 ml of 2N aqueous sodium hydroxide solution and a solution of 13.5 ml (0.19 mole) of acetyl chloride in 150 ml of chloroform were added dropwise, alternatively, with 2.5 ml portions of the former and 5 ml portions of the latter.

After completion of the addition, the mixture was stirred at 0° to 2° C. for 30 minutes and then at room temperature for an hour. The chloroform layer was removed and the aqueous layer was adjusted to pH 2 by adding 75 ml of 4N hydrochloric acid. The mixture was saturated with ammonium sulfate, and the resulting precipitate was collected by filtration, washed with water, dried and recrystallized from water to give 27.63 g of N-acetyladrenalone.

m.p. 175°–176° C.

To 98 g (0.7 mole) of anhydrous potassium carbonate were added 150 ml of N,N-dimethylformamide and 335 ml of dichloromethane, and a solution of 22.32 g (0.1 mole) of N-acetyladrenalone obtained above in 150 ml of N,N-dimethylformamide was added dropwise at reflux under a nitrogen atmosphere. Reflux was continued until the disappearance of the spot of the starting material was recognized by means of silica gel thin layer chromatography, and then the solution was allowed to stand overnight. The insolubles were removed by filtration, the filtrate was concentrated under reduced pressure, and the residue was dissolved in dichloromethane, washed successively with a saturated aqueous sodium chloride solution, 0.25% aqueous sodium hydroxide solution and a saturated aqueous sodium chloride solution and dried. The solution was evaporated and the residue was applied to silica gel column chromatography (eluent; dichloromethane:isopropyl alcohol=100:1). The fractions having a single spot were combined and concentrated, and the residue was recrystallized from ethanol:water (1:1.5) to give 14.24 g of the title compound.

m.p. 99°–100° C.

NMR (CDCl$_3$) $\delta$ (ppm);2.04, 2.24 (2s, 3H), 3.05, 3.16 (2s, 3H), 4.76, 4.86 (2s, 2H), 6.16, 6.18 (2s, 2H), 6.92–7.76 (m, 3H).

MS (m/e); 235 (M+), 44 (base).

Following a process similar to that of Example 1, there was obtained N-methyl-N-(3,4-methylenedioxyphenacyl)-n-hexanamide.

m.p. 69°–70° C.

NMR (CDCl$_3$) $\delta$ (ppm); 0.94 (t, 3H), 1.34 (m, 4H), 1.70 (m, 2H), 2.40 (m, 2H), 3.04, 3.14 (2s, 3H), 4.76, 4.82 (2s, 2H), 6.14 (s, 2H), 6.94 (m, 1H), 7.64 (m, 2H).

MS (m/e); 291 (M+), 44 (base).

EXAMPLE 2

Preparation of N-methyl-N-(3,4-methylenedioxyphenacyl)acetamide.

To a solution of 65.6 g (0.27 mole) of α-bromo-3,4-methylenedioxyacetophenone in 530 ml of ethanol was added dropwise 160 ml of 40% aqueous methylamine solution at 5° C. Then, 85.3 g (1.08 mole) of pyridine was added, and then 82.6 g (0.81 mole) of acetic anhydride was added dropwise at 5° C. The mixture was gradually raised to room temperature and allowed to stand overnight. The ethanol was evaporated, and the residue, after addition of ice water, was extracted with dichloromethane. The dichloromethane layer was washed with water, dried and concentrated to give a viscous oil, which was then applied to silica gel column chromatography (eluent: ethyl acetate) to give 27.0 g of the title compound.

m.p. 99°–101° C. (recrystallized from n-hexane-ethyl acetate).

EXAMPLE 3

Preparation of N-(3,4-methylenedioxyphenacyl)acetamide

To a solution of 7.01 g (0.55 mole) of hexamethylenetetramine in 80 ml of chloroform cooled on ice was added dropwise a solution of 12.16 g (0.05 mole) of α-bromo-3,4-methylenedioxyacetophenone in 70 ml of chloroform to precipitate a white solid. After standing for 24 hours, the precipitating solid was collected by filtration and washed with chloroform to give 18.46 g of a quaternary ammonium salt.

m.p. 159°–159.5° C. (decomposition).

To a mixture of 150 ml of ethanol and 15 ml of conc. hydrochloric acid was gradually added the quaternary ammonium salt obtained above, and the mixture was stirred at 45° to 50° C. for 10 minutes to give a granulated solid. After standing overnight, the precipitating solid was collected by filtration and washed with ether to give 17 g of a primary ammonium salt.

To a cooled (5° C.) solution of 3.5 g of (0.01 mole equivalent) of the primary ammonium salt in water was added 10 ml (0.1 mole) of acetic anhydride, followed by the gradual addition of 20 g (0.24 mole) of anhydrous sodium hydrogen carbonate, and the mixture was stirred at room temperature for 3 hours. The precipitating solid was collected by filtration, and the filtrate was extracted with dichloromethane. The solid collected by filtration and the extract were combined, washed successively with 4N hydrochloric acid, 5% aqueous sodium hydrogen carbonate solution and a saturated aqueous sodium chloride solution and dried. The solvent was evaporated, and the resulting solid was recrystallized from 50% ethanol to give 1.6 g of the title compound.

m.p. 152°–153.5° C.

NMR (CDCl$_3$) $\delta$ (ppm); 2.14 (s, 3H), 4.72, 4.78 (2s, 2H), 6.16 (s, 2H), 6.62 (br, 1H), 6.97–7.70 (m, 3H).

MS (m/e); 221 (M+), 149 (base).

Following a process similar to that of Example 3, there were obtained the following compounds.

N-(3,4-methylenedioxyphenacyl)-n-butanamide m.p. 107°–108° C. (recrystallized from ethanol-water).

NMR (CDCl$_3$) $\delta$ (ppm); 1.01 (t, 3H), 1.77 (m, 2H), 2.32, 2.34 (2t, 2H), 4.74, 4.78 (2s, 2H), 6.16 (s, 2H), 6.62 (br, 1H), 6.98–7.70 (m, 3H).

MS (m/e); 249 (M+), 149 (base).

N-(3,4-methylenedioxyphenacyl)-n-hexanamide m.p. 110.5°–112° C. (recrystallized from ethanol-water).

NMR (CDCl$_3$) $\delta$ (ppm); 0.93 (t, 3H), 1.38 (m, 4H), 1.70 (m, 2H), 2.35 (t, 2H), 4.76 (d, 2H), 6.16 (s, 2H), 6.62 (br, 1H), 6.98–7.70 (m, 3H).

MS (m/e); 277 (M+), 149 (base).

EXAMPLE 4

Preparation of N-(β-hydroxy-3,4-methylenedioxyphenethyl)-N-methylacetamide

To a solution of 0.47 g (0.002 mole) of N-methyl-N-(3,4-methylenedioxyhenacyl)acetamide in 20 ml of ethanol cooled on ice was added gradually 0.227 g (0.006 mole) of sodium borohydride, and the mixture was stirred for 1.5 hours. The insolubles were removed by filtration, and the filtrate was concentrated. The residue was dissolved in water, saturated with sodium chloride and extracted with dichloromethane. The extract was washed with a saturated aqueous sodium chloride solution, dried and concentrated to give a solid, which was then recrystallized from ethyl acetate to give 0.41 g of the title compound.

m.p. 111°–112° C.

NMR (CDCl$_3$) δ (ppm); 2.16 (s, 3H), 2.98 (s, 3H), 3.66 (m, 3H), 4.94 (q, 1H), 6.04 (s, 2H), 6.90 (s, 2H), 6.98 (s, 1H).

MS (m/e); 237 (M+), 44 (base).

TEST EXAMPLE 1

Effect on acute liver injury induced by carbon tetrachloride

Ten male ICR strain mice (six weeks old, about 30 g of body weight) per group were used for the test. Suspensions of the compound, obtained in Example 1, in 5% gum arabic solution in various concentrations were prepared for test drugs. A 5% gum arabic solution was used as a control. The test drugs and a 5% gum arabic solution were each administered orally in an amount of 10 ml/kg of body weight to different animals. After standing for 18 hours, the animals were anesthetized with ether, the blood was drawn and centrifuged for measuring the serum GPT value. Malotilate served as a comparative test drug. The results are shown in Table 1.

TABLE 1

| Effect on acute liver injury induced by carbon tetrachloride | | | |
|---|---|---|---|
| Group | Dose (mg/kg) | (GPT (IU/1)* | Inhibition % |
| Control | — | 5945 ± 598 | — |
| A | 10 | 2634 ± 380 | 56 |
|  | 30 | 636 ± 245 | 89 |
|  | 100 | 39 ± 3 | 100 |
| B | 10 | 4291 ± 1012 | 28 |
|  | 30 | 1778 ± 310 | 71 |
|  | 100 | 148 ± 40 | 98 |

A: The compound obtained in Example 1
B: Malotilate
*: mean ± S.E.

TEST EXAMPLE 2

Effect on acute liver injury induced by D-galactosamine

Six male Wister strain rats (eight weeks old, about 200 g of body weight) per group were used for the test. Suspensions of the compound, obtained in Example 1, in 5% gum arabic solution in various concentrations were prepared for test drugs. A 5% gum arabic solution was used as a control. The test drugs and a 5% gum arabic solution were each administered orally in an amount of 5 ml/kg of body weight to different animals. After standing for 18 hours, the animals were anesthetized with ether, the blood was drawn and centrifuged for measuring the serum GPT value. Malotilate served as a comparative test drug. The results are shown in Table 2.

TABLE 2

| Effect on acute liver injury induced by D-galactosamine | | | |
|---|---|---|---|
| Group | Dose (mg/kg) | GPT (IU/1)* | Inhibition % |
| Control | — | 20606 ± 1750 | — |
| A | 30 | 15972 ± 2810 | 22.5 |
|  | 100 | 7440 ± 757 | 64.1 |
|  | 300 | 4415 ± 1539 | 78.8 |
| B | 30 | 19240 ± 1183 | 6.4 |
|  | 100 | 11190 ± 777 | 45.6 |
|  | 300 | 15557 ± 1669 | 24.6 |

A: The compound obtained in Example 1
B: Malotilate
*: mean ± S.E.

What is claimed is:

1. An N-substituted amide derivative represented by the formula

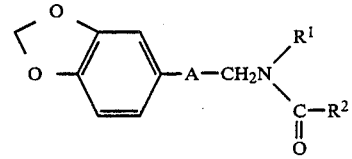

wherein A is —CH(OH)— or —C(=O)—, $R^1$ is a hydrogen atom or an alkyl group having 1 to 3 carbon atoms, and $R^2$ is an alkyl group having 1 to 6 carbon atoms.

2. N-(3,4-methylenedioxyphenacyl)acetamide.
3. N-methyl-(3,4-methylenedioxyphenacyl)acetamide.
4. N-methyl-(3,4-methylenedioxyphenacyl)-n-hexanamide.
5. N-(3,4-methylenedioxyphenacyl)-n-butanamide.
6. N-(3,4-methylenedioxyphenacyl)-n-hexanamide.
7. N-methyl-N-(β-hydroxy-3,4-methylenedioxyphenethyl)acetamide.

* * * * *